United States Patent [19]

Lisec

[11] Patent Number: 5,335,012

[45] Date of Patent: Aug. 2, 1994

[54] APPARATUS FOR INSPECTING THE SEAL OF INSULATING GLASS PANES

[76] Inventor: Peter Lisec, Bahnhofstrasse 34, A-3363 Amstetten-Hausmening, Austria

[21] Appl. No.: 944,991

[22] Filed: Sep. 15, 1992

[30] Foreign Application Priority Data

Sep. 16, 1991 [AT] Austria .................................. 1858/91

[51] Int. Cl.⁵ ............................................. H04N 7/18
[52] U.S. Cl. ...................................... 348/92; 348/132
[58] Field of Search ................ 358/93, 101, 106, 107; 65/29; 382/8; H04N 7/18

[56] References Cited

U.S. PATENT DOCUMENTS

| | | | |
|---|---|---|---|
| 4,319,270 | 3/1982 | Kimura | 358/106 |
| 4,666,492 | 5/1987 | Thimons | 65/29 |
| 4,758,888 | 7/1988 | Lapidot | 358/106 |
| 4,816,052 | 3/1989 | Horvath | 65/29 |
| 4,853,776 | 8/1989 | Itaya | 358/106 |
| 4,918,522 | 4/1990 | Pajunen | 358/106 |
| 5,016,099 | 5/1991 | Bongardt | 358/106 |

*Primary Examiner*—Howard W. Britton
*Attorney, Agent, or Firm*—Young & Thompson

[57] ABSTRACT

An apparatus for conveying sealed insulating glass panes (1) includes a conveying device (3, 14) associated, in the zone of the end (10) on the inlet side and the end (11) on the outlet side, with recorders (12), preferably those with respectively two TV cameras, producing images of the corners (4, 5, 6, 7) of the insulating glass pane (1), these images being displayed as stationary images on a monitor (41) until the subsequent insulating glass pane (1) arrives. In order to improve the quality of the images, illuminating devices (15) are associated with the recorders (12), these devices being activated only when the recorders (12) are in operation. Based on the images of the corners (4 and 5) of the insulating glass pane (1) produced by the recorders (12) and displayed on the monitor (41), the quality of the seal (20) in the zone of the corners (4, 5, 6, 7) can be evaluated even without lifting out and turning of insulating glass panes (1).

20 Claims, 6 Drawing Sheets

APPARATUS FOR INSPECTING THE SEAL OF INSULATING GLASS PANES

The invention relates to an arrangement for testing the seal of insulating glass panes in the zone of corners of an insulating glass pane.

In modern insulating glass production lines, sealing of insulating glass panes, i.e. filling the edge joint of an insulating glass blank, defined laterally by the rims of the two glass panes and inwardly by spacer frames, with a sealing compound (usually a curable bicomponent plastic composition based on polysulfide), is normally performed by sealing devices equipped with one or two filling nozzles (sealing nozzles) from which the sealant is introduced into the edge joint.

In these conventional sealing facilities, the work is usually performed on insulating glass pane blanks which are aligned in substantially perpendicular standing position. It is thus necessary, for controlling the quality of the seal in the corner zone—this being a zone wherein the seal is deficient under certain circumstances because at that point the sealing nozzles are pivoted by 90°, or the sealing step is commenced, or terminated—that the insulating glass panes be turned before being deposited, after removal from the delivery conveyor of the sealing facility, on a supporting trestle to allow the seal to cure.

This turning over of the insulating glass panes for controlling the sealing quality in the corner zone can be executed, in case of relatively large insulating glass panes, only by two persons and, in case of extremely large insulating glass panes, actually only with the use of suitable hoisting tools. For this reason, testing of the quality of the seal in the corner zone, especially in the region of the lower corners abutting the delivery conveyor of the sealing facility, is frequently simply omitted.

Sealing facilities have been known from German Patent 2,816,437, 2,846,785, German Utility G 89 04 381.2, DOS 4,009,436, and DOS 4,009,441. Conveyors as they can be used with special advantage in conjunction with sealing devices, particularly for carrying away the sealed insulating glass panes without impairing or contacting the sealant which at that point is not as yet cured, have been known from DOS 3,038,425 or from EP-A-0,123,009.

The invention is based on the object of indicating an arrangement of the type described above making it possible to perform the checking of the seal of insulating glass panes in the zone of the corners located at the bottom during the delivery by the outlet conveyor of the sealing facility without lifting out and turning of the insulating glass panes. In this connection, the apparatus is not to be limited to a specific structure of a delivery conveyor but rather is to be usable in any type of constructions of conveyors.

According to the invention, this object has been attained by providing at least one recorder, especially a television camera, located in the region of the delivery conveyor of a sealing facility, and at least one monitor connected with the at least one recorder for displaying the images of corners of the insulating glass pane detected by the recorder.

Recorders, especially TV cameras, for the testing of workpieces are known per se. Thus, DOS 3,809,221 describes a method for the detection of flaws of workpieces including an optical illuminating device and an optical receiver system for recording the illuminated surface region, adjusted with respect to each other and to the surface region of the workpiece in such a way that differing reflective properties of flaws in the surface region as compared with their surrounding area become apparent during the generation of an image. The procedure herein, in detail, is such that an image of the surface region is recorded in picture dots and is then compared with a reference image. It is also possible to provide a storage means wherein the reference image is retained.

DOS 3,144,379 describes a process for performing testing for fissures in test specimens, samples of material, or building parts, wherein the surface to be investigated is covered with a thin layer of a transparent varnish tearing together with the testing specimen. The testing specimen is then placed under a load, and the measuring site is illuminated by the illuminating device at an angle different from the viewing angle of the recorder. The objective of this procedure resides in avoiding this necessary, expensive high polishing of the surface of the specimen.

DOS 2,648,694 discloses a process and an apparatus for testing semifinished products wherein several surface areas of the semifinished product are to be scanned by one or several television cameras so that the lines of the video images run approximately perpendicularly to the direction of motion of the semifinished product. This arrangement includes a device for obtaining line section signals. There is no disclosure in DOS 2,648,694 with regard to the type and design of the illuminating device and its alignment with respect to the television camera.

In GB-A-2,144,533, a television camera is connected on the output side to the input of a comparator. In this system, the video signal is to be compared with a predetermined threshold value. As a practical example, the examination of meat for its fat content is described wherein two components are to be used which are to recognize meat, on the one hand, and fat, on the other hand.

Although television cameras for the testing of materials have been known per se, the special application to testing of the sealing quality in the corner zone of insulating glass panes according to the invention has not been obvious from the state of the art.

By means of the arrangement according to this invention, the at least one recorder records at least one image which is displayed by a monitor. The operator of the sealing facility thus can visually examine without difficulties also the corners of insulating glass panes located at the bottom, and determine whether the seal in the corner zone is smoothly and properly executed (without flaws, such as cavities or the like) and does not exhibit, for example, depressions or other irregularities. The monitor is located, in the arrangement of this invention, preferably in the region of the control desk or, even more preferably, at the outlet end of the delivery conveyor or beside the substantially vertical rim of the rearward support, provided at that location, of the sealing facility delivery conveyor, namely preferably at eye level.

Even though basically the apparatus of this invention can function adequately with a recorder providing images first of one lower corner and then of the other lower corner of the insulating glass pane, an embodiment is given preference wherein a recorder is provided in the interruption beside the beginning of the delivery conveyor through which a sealing nozzle moves from a ready position into its operative position and wherein a further recorder is located in the zone of the outlet end of the delivery conveyor of the sealing apparatus. This embodiment has the advantage that for each corner at least one separate recorder is provided so that the respectively most favorable viewing angle can be chosen for the recorders. In this arrangement, a separate monitor can be included for each recorder or, alternatively, the field of the monitor is subdivided in correspondence with the number of recorders—normally two—(i.e., it is essentially bisected).

A favorable viewing angle results if the recorder is arranged at a lower level than the delivery conveyor. In this case, it is especially preferred to mount the recorder with a viewing direction forming an acute angle with the plane of the insulating glass pane. For it has been found that, using such a viewing angle, unevennesses and depressions in the seal are imaged especially "plastically".

It proved to be advantageous to equip the, or each, recorder with two TV cameras. Here the possibility offers itself to align the TV cameras from mutually opposite sides of the insulating glass pane under an acute angle with respect to the plane of the insulating glass pane so that their viewing angles are oriented toward respectively one rim, i.e. the particularly critical zone, of the seal in the corner region. In this connection, each TV camera is preferably oriented toward the edge of the seal lying farther remote therefrom (patent claim 13): Preferred features of this preferred embodiment of the invention are the subject matter of claims 10-13.

The invention also includes the feature that a control unit is provided which triggers the generation of an image by the recorder located in the region of the end on the inlet side of the delivery conveyor when the insulating glass pane is at a standstill after termination of the sealing process and before commencing the carry-away step by the delivery conveyor.

Analogously, the provision can be made within the scope of the invention that a control unit is included triggering the production of an image by the recorder located at the end on the outlet side of the delivery conveyor when the insulating glass pane is in the removal position at the end of the delivery conveyor. In this way, the images are recorded by the recorders at the respectively correct instant, namely when the corner of the insulating glass pane to be recorded and to be imaged at that moment projects past one end or the other end of the delivery conveyor.

In order to be able to perform an examination of the images produced on the monitor at leisure, it is preferred within the scope of this invention that the thus-generated images are frozen images displayed on the monitor or monitors until the subsequent insulating glass pane arrives to be sealed.

In a practical embodiment of the invention, the provision can be made that the control unit exhibits a device, for example a light barrier, a proximity switch, or the like, for detecting the insulating glass pane, this device activating the first recorder when the corner of the insulating glass pane to be imaged thereby, being the rearward one based on the conveying direction, is located in the zone of the end of the delivery conveyor on the inlet side. Analogously, the additional provision can be made within the scope of this invention that the control unit includes a means, for example a light barrier, a proximity switch, or the like, for detecting the insulating glass pane, this means activating the recorder when the corner of the insulating glass pane to be imaged thereby, being the forward one based on the conveying direction, is located in the zone of the end of the delivery conveyor on the outlet side.

The image produced on the monitor, or the images produced on the monitor (in case two or more recorders are provided, or recorders with two TV cameras each are included), can remain "frozen" without disadvantage until the subsequent corners of the insulating glass pane are to be imaged. It is thus recommended within the scope of the invention to use an embodiment encompassing a device, for example a light barrier, a proximity switch, or the like, for detecting the incoming of the next insulating glass pane to be sealed, which triggers the clearing of the image or images, displayed on the monitor, of corners of the previously sealed insulating glass pane.

In a practical embodiment of the invention, the provision is made that especially the recorder located in the region of the sealing nozzle is associated with a lid protecting the optical system of this recorder, this lid being opened exclusively during the taking of an image. This embodiment proves itself well especially since the possibility can never be entirely excluded in sealing devices, even if these are very accurately controlled, that sealant will drip from the sealing nozzle or the sealing nozzles and reach the recording device.

Especially in case of unfavorable lighting conditions in the building wherein the sealing station is set up, an embodiment of the invention has proven to be advantageous wherein the provision is made that at least one illuminating device is associated with the recorder, illuminating the corner to be imaged at an angle different from the angle formed by the viewing direction of the recording device with the plane of the insulating glass pane.

The provision of a separate illuminating device makes it possible to set the respectively most favorable illuminating conditions for imaging the corners and to do this independently of the lighting conditions otherwise prevailing in the building.

Since it is unnecessary in this invention to have the illuminating device associated with the recorders or the recorder constantly in operation, the provision can be made that the illuminating device is coupled with the control of the recorder with inclusion of the device for detecting the presence of an insulating glass pane; in this arrangement, the illuminating device is turned on only while a recording is being made. Particularly in this embodiment, the provision can be made that the illuminating device has a flash unit as the lighting source.

As mentioned above, an embodiment of the arrangement according to this invention is preferred wherein two recorders are included. Ordinarily, this will be sufficient since the corners of the insulating glass panes located at the top in the removal position can also be tested visually without any special auxiliary means.

However, when using, for unloading the sealing facility, automatically operating means (unloading robots or automatic unloading machines), operating personnel must not be present in the region of the unloading robot. For this reason, the provision is made according to a suggestion advanced by the invention that especially in case of a sealing facility equipped with an automatic unloading machine or robot at least two additional recorders are included for observing the upper corners of the sealed insulating glass panes.

In this connection, the feature has proved to be of advantage that the recorders and the illuminating devices optionally associated therewith are mounted on a beam that can be shifted upwards and downwards, this beam carrying freely rotatable rollers on which the upper rim of the sealed insulating glass pane to be removed is supported. Such a beam has been known, for example, from DOS 3,038,425, Austrian Patent 370,201, or Austrian Patent 370,706 in conjunction with assembly stations for insulating glass panes.

Additional details and features of the invention can be seen from the following description, reference being had to the drawings wherein embodiments of the invention are illustrated in partially schematic views. In the drawings.

The arrangement of this invention is usually associated with delivery conveyors for automatic sealing facilities of insulating glass panes. These automatic sealing facilities can exhibit a structure as known from the above-cited references, or they can also be constructed in accordance with EP-A-391,884.

Figure 1:
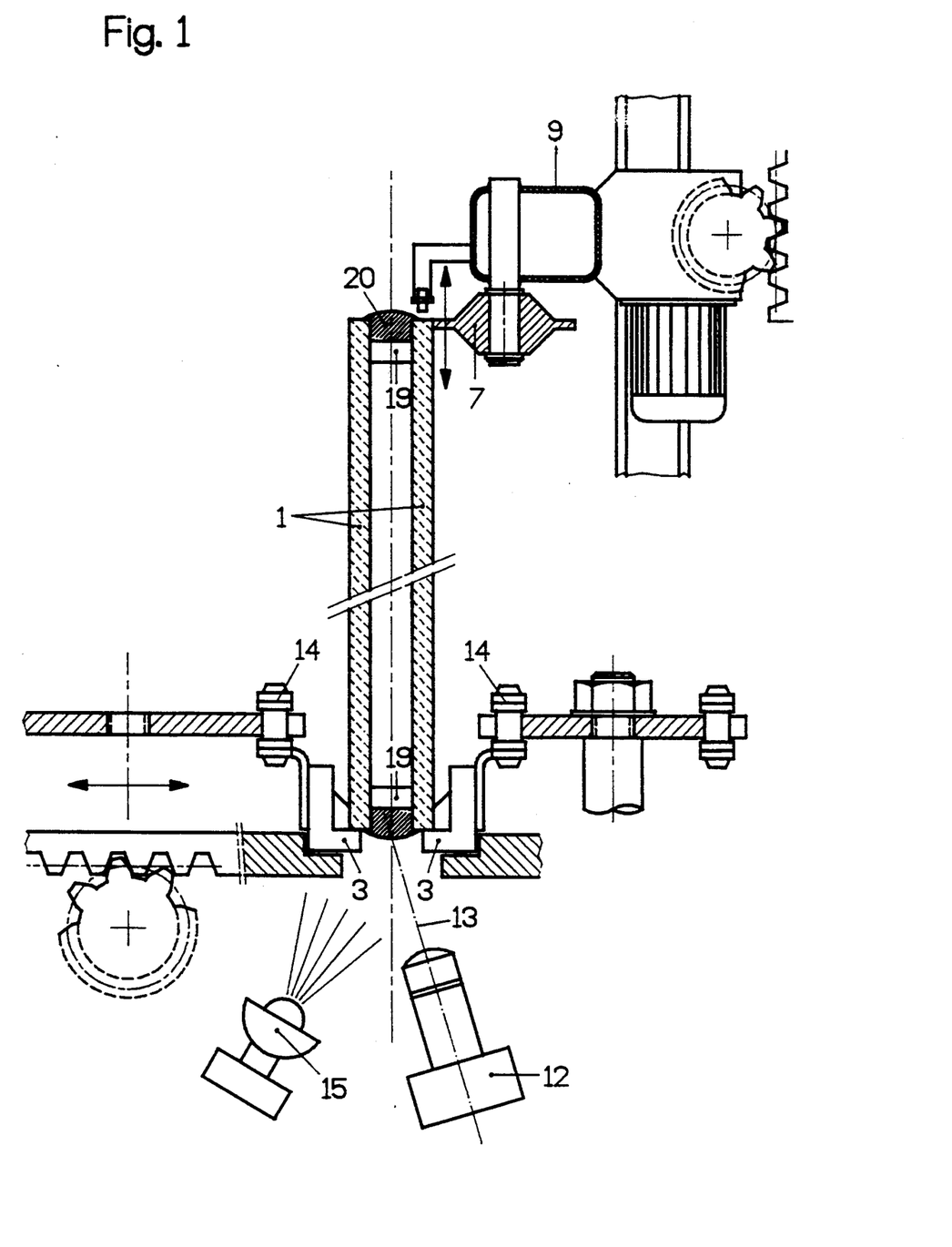
FIG. 1 shows a delivery conveyor for sealed insulating glass panes of the type of structure known from DOS 3,038,425, the arrangement according to this invention being included therein.
Figure 2:
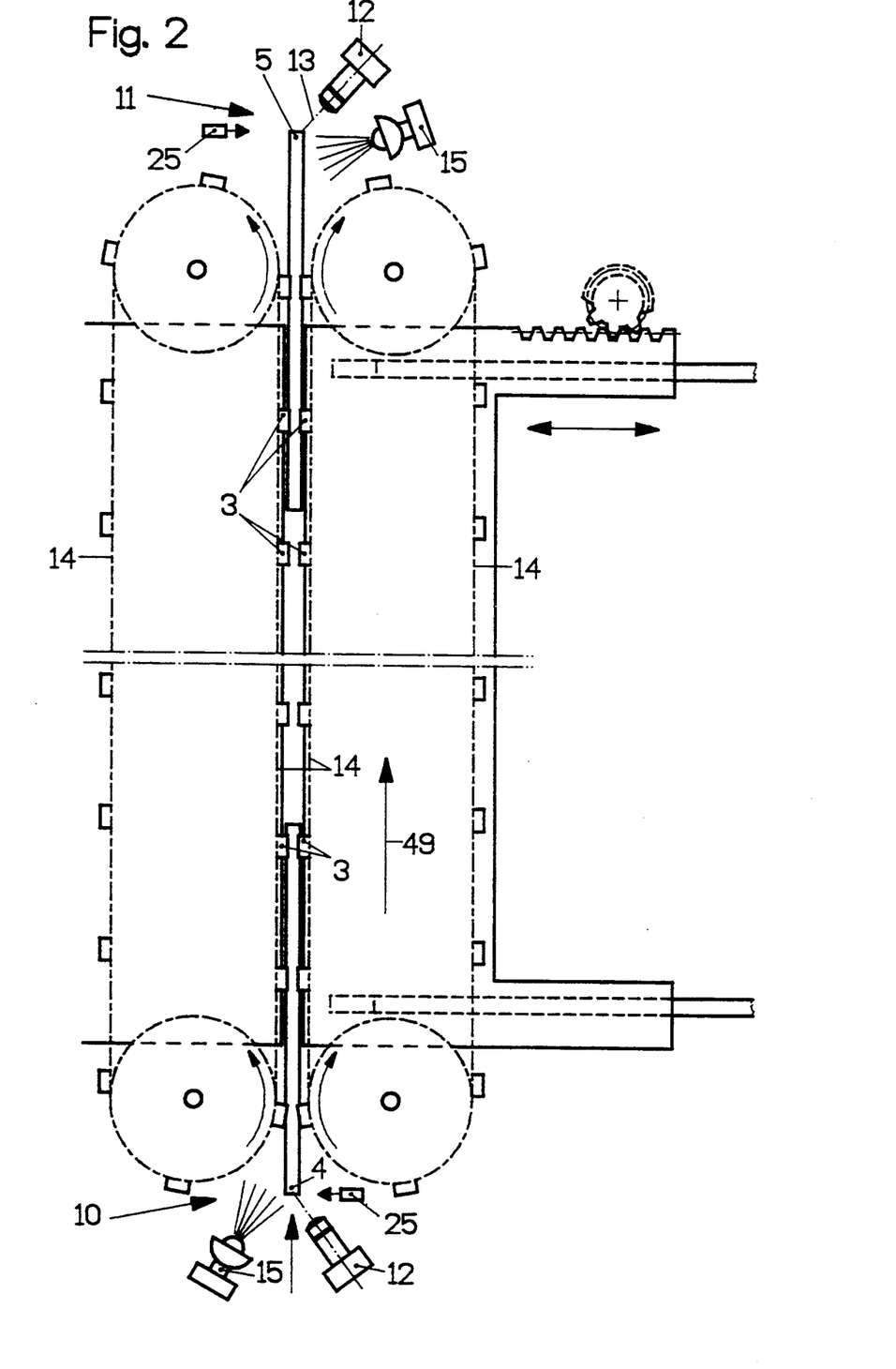
FIG. 2 shows the delivery conveyor of FIG. 1 in a top view.

As illustrated in FIGS. 1 and 2, the delivery conveyor has the structure as known, for example, from DOS 3,038,425. In this system, an insulating glass pane 1, the edge joint of which, defined by the rims of the glass panes toward the side and by a spacer frame 19 toward the inside, is filled with sealing compound 20, is supported and moved at the bottom by hook-shaped supports 3 attached to endless chains 14. Freely rotatable supporting rollers 7, engaging at a beam 9 that can be moved upwards and downwards with the aid of a drive mechanism, are provided in the zone of the upper rim of the insulating glass pane 1. In place of the beam 9 with the supporting rollers 7, it is also possible to arrange another lateral support, for example a field of rollers or an air-cushion wall.

As schematically indicated in FIGS. 1 and 2, a recorder 12, designed, for example, as a television camera, is associated in each case with the ends of the delivery conveyor shown in FIGS. 1 and 2, i.e. with the end 10 on the inlet side and the end 11 on the outlet side.

The recorder 12 is arranged so that its viewing direction 13 (indicated in FIGS. 1 and 2 by a dot-dash line) is oriented obliquely from the bottom, i.e. at an angle acute with respect to the plane of the insulating glass pane 1, onto the corner 4 or 5 of the insulating glass pane 1 located in each case in the proximity of the recording device 12.

The ends 10 and 11, respectively, of the delivery conveyor are additionally associated with illuminating devices 15 in order to correspondingly illuminate the corner 4 or 5, i.e. the forward corner 5 and the rearward corner 4, based on the conveying direction (arrow 49), for being recorded by the recorders 12. These illuminating devices 15 preferably form an angle with the plane of the insulating glass pane 1 which is different from that of the recorders 12. The illuminating devices 15 can have, as the light sources, normal light bulbs, low-voltage bulbs, or halogen bulbs, or they can be flash units emitting light only at the instant of recording, i.e. when the corner 4 is located at the inlet 10 of the delivery conveyor, or the corner 5 is disposed at the end 11 of the delivery conveyor.

Figure 3:
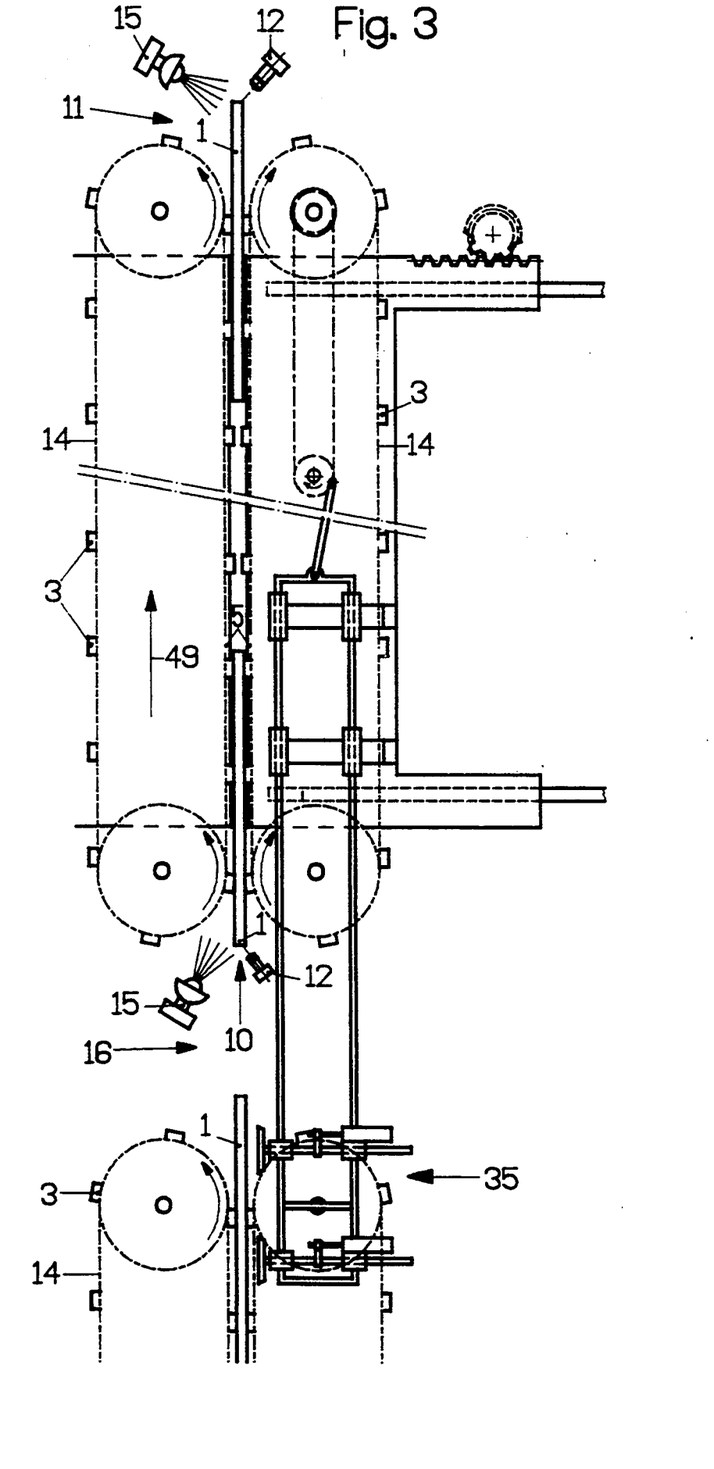
FIG. 3 shows a delivery conveyor of the type known from EP-A-0,123,009 wherein the arrangement of this invention is provided.

The structure described in connection with FIGS. 1 and 2 also applies to the conveying device, equipped with an auxiliary conveyor 35, known from EP-A-0,123,009. FIG. 3 shows additionally the interruption between the two conveyor path sections, namely the gap 16 wherein a sealing nozzle (not illustrated) moves up and down perpendicularly to the image plane of FIG. 3, or moves into a position for filling the vertically aligned edge joints and the lower horizontal edge joint of insulating glass panes 1 with sealing compound 20.

As described above, recorders 12 and illuminating devices 15 associated therewith are provided on at least one end of the delivery conveyor, but preferably, as illustrated, on both ends 10 and 11 of the delivery conveyor. In order to activate the recorders and optionally the illuminating devices 15 correspondingly, i.e. to trigger them or render them operative whenever a corner 4 or 5 is at the beginning 10 or at the end 11 of the delivery conveyor, it is possible to include sensors 25, as shown in FIGS. 2 and 4 (the sensors are, for example, proximity switches, light barriers, or similar noncontactually responding sensors, or also simple mechanical switches); these sensors detect the presence of the corners 4 and 5, respectively.

Figure 4:
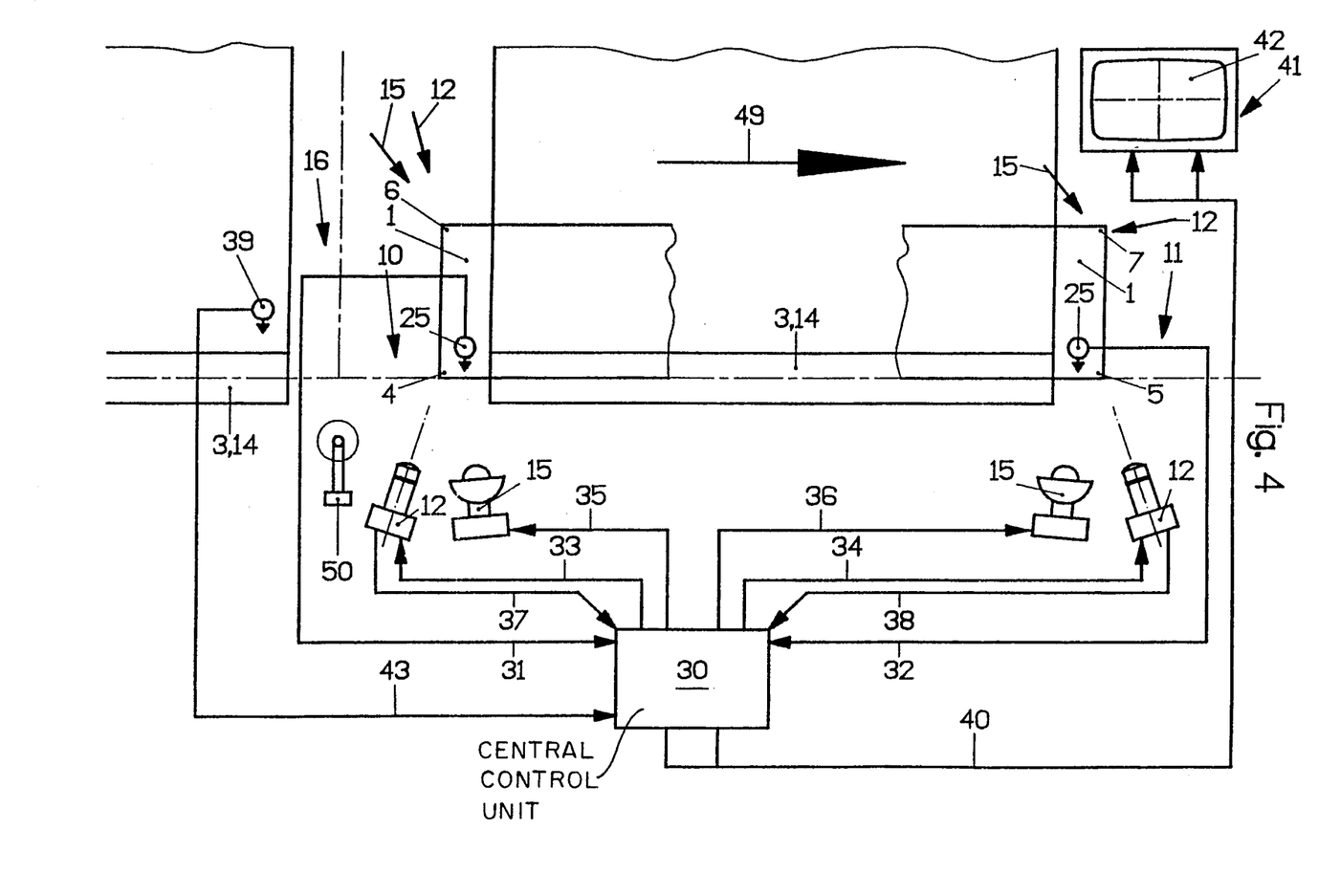
FIG. 4 shows schematically an arrangement according to this invention in the region of a delivery conveyor, including the control system for the arrangement of this invention.

As shown in FIG. 4, the arrangement of this invention comprises a central control unit 30. Signals are fed to this control unit 30 once one of the sensors 25 has picked up a corner 4 or 5 of an insulating glass pane 1 located at the beginning 10 or, respectively, at the end 11 of the delivery conveyor. For this purpose, the sensors 25 are connected to the central unit 30 via control lines 31, 32. The central unit 30 transmits, via control lines 33, 35, a command to the recorder 12 and the illuminating unit 15 associated with the end 10 of the delivery conveyor in order to produce an image of the corner 4 of the insulating glass pane 1 located in the zone of the end 10. Analogously, the illuminating device 15 and the recorder 12 in the zone of the end 11 of the delivery conveyor are actuated by way of control lines 34, 36 when the sensor 25 provided in the area of the end 11 determines the presence of the corner 5 of the insulating glass pane 1 at the end 11 on the outlet side.

The image signals produced by the recorders are transmitted to the central unit 30 via lines 37 and 38, respectively. The central unit 30 then transmits, via a signal line 40, the image signals to a monitor 41 which latter, in the illustrated embodiment, exhibits a screen 42 subdivided into four fields. The monitor 41 includes four fields because, in the embodiment of FIG. 4, recorders 12 and illuminating devices 15 are also associated with the upper corners 6 and 7 of the insulating glass pane 1. These recorders 12 and the illuminating devices 15 illuminating and, respectively, imaging the corners 6 and 7 are advantageously mounted to the beam 9 shown in FIG. 1, carrying the freely rotatable supporting rollers 7, so that they are in each case oriented at the correct level with respect to the corners 6 and 7 of the insulating glass pane 1.

In case the recorders 12 and the illuminating devices 15, indicated in FIG. 4 merely by symbolic arrows, are not provided in the zone of the upper corners 6 and 7 of the insulating glass pane 1, it is sufficient to divide the screen 42 of the monitor 41 into merely two halves, preferably two juxtaposed halves, and to represent, as a frozen image, in one half, preferably in the left-hand half in FIG. 4, the image of the corner 4 and, in the right-hand half of the screen 42, the image of the corner 5 of the insulating glass pane 1.

Furthermore, a sensor 39 is included in FIG. 4, connected to the central unit 30 by way of a control line 43. The sensor 39 detects the introduction of the subsequent insulating glass pane 1 into the region of the interruption 16 of the conveying devices 3, 14, the sealing nozzle 50 being located in this interruption in its waiting position (ready position), so that the central unit 30 prepares, based on the signal received via the line 43, the recorders 12 and the illuminating devices 15 for imaging the subsequent corners 4, 5 (and optionally the corners 6 and 7) of the next following insulating glass pane 1, and clears the images, thus far displayed on the monitor 41, of the corners 4, 5 (and optionally the corners 6 and 7) of the preceding insulating glass pane 1, as well as the memory for these images in the central unit 30.

Figure 5:
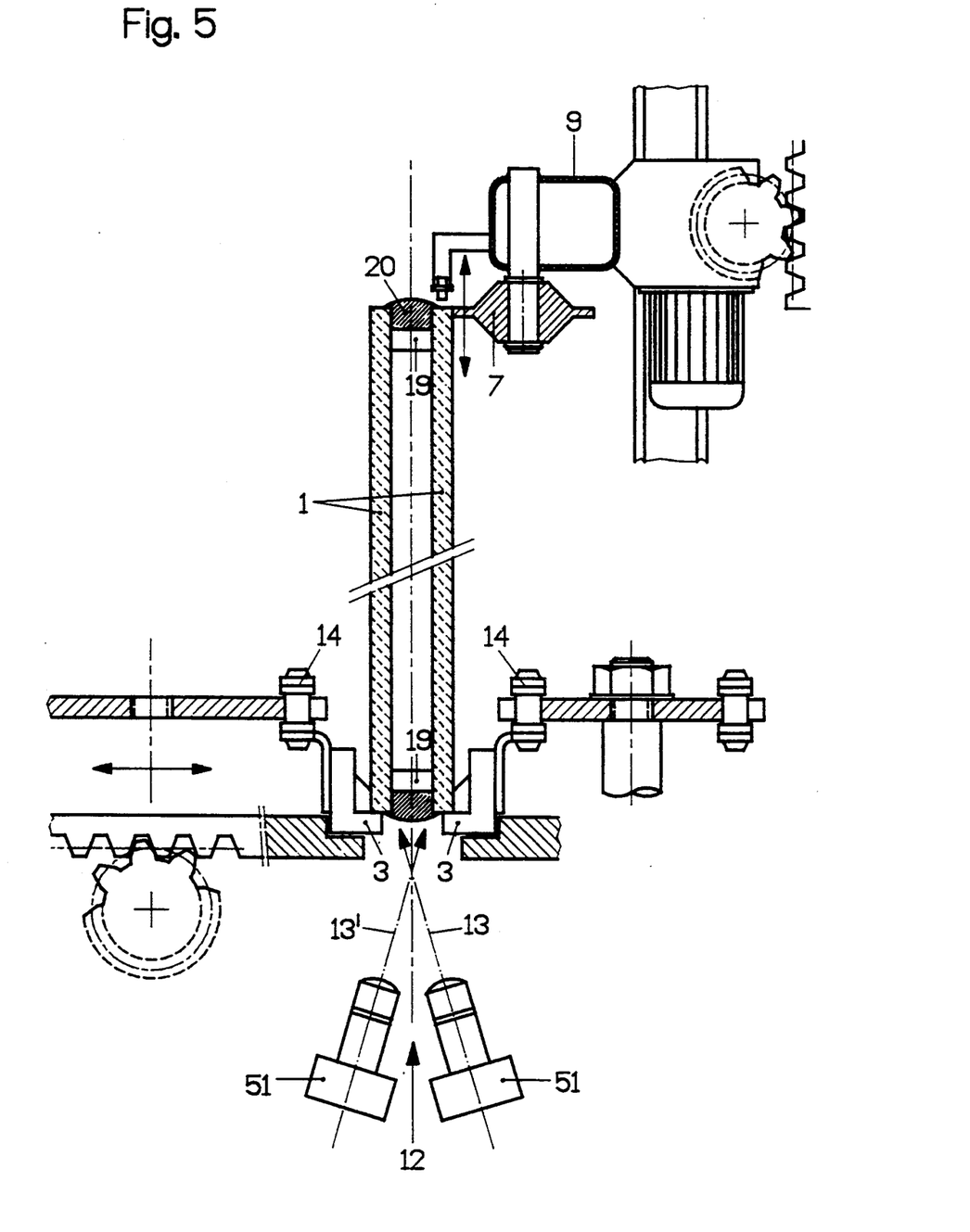
FIG. 5 is an embodiment with two TV cameras per recorder.
Figure 6:
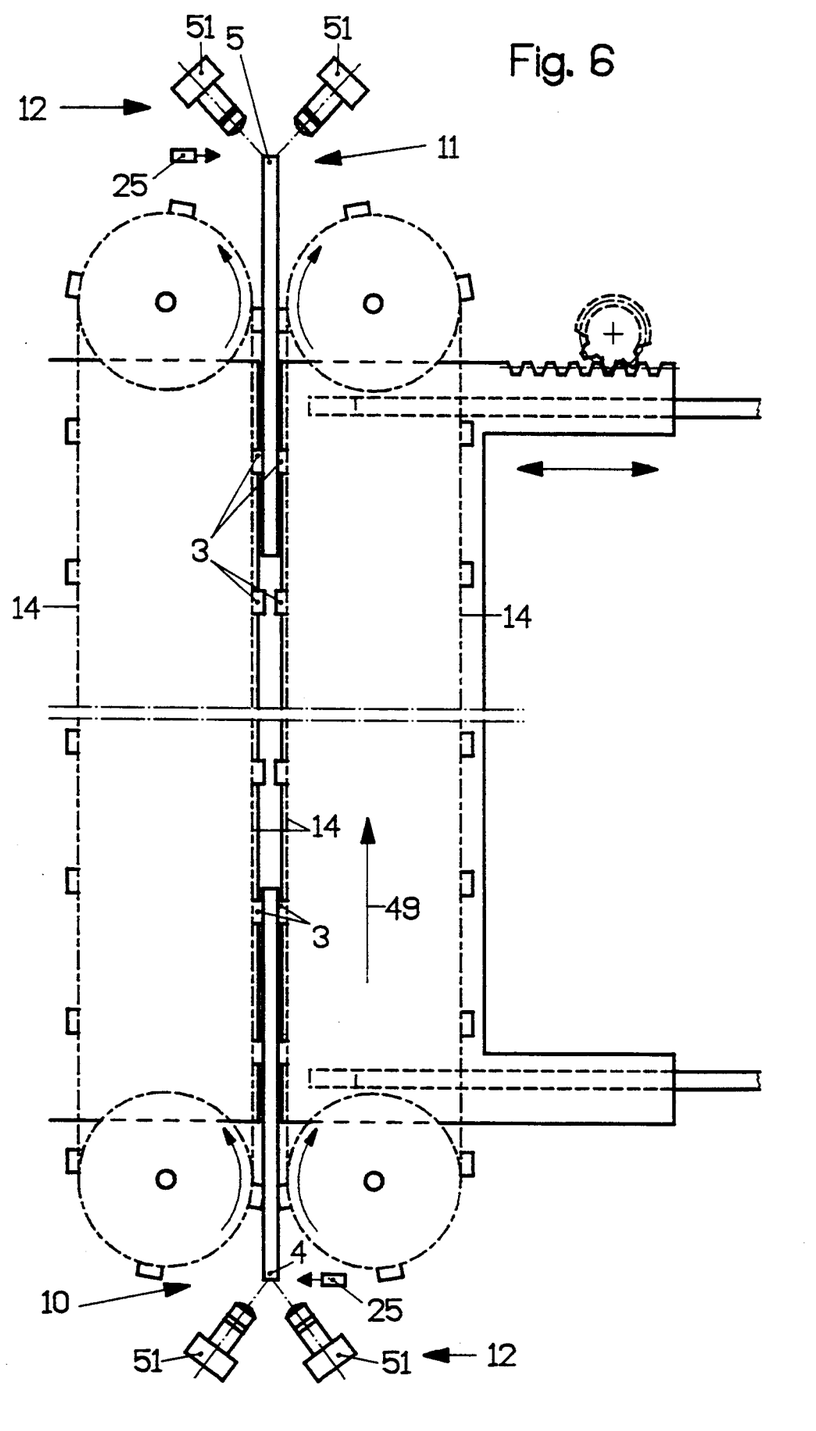
FIG. 6 is a top view thereof.

In FIGS. 5 and 6, an embodiment of the arrangement according to this invention is shown wherein the at least one recorder 12 exhibits two TV cameras 51 oriented at differing viewing directions 13, 13' onto the seal 20 in the edge joint of the insulating glass pane 1 to be monitored. As shown in FIG. 6, such recorders with two TV cameras can be provided at the end 10 on the inlet side as well as at the end 11 on the outlet side of the conveyor. It is understood that recording devices 12 with two TV cameras 51 can also be arranged so that they are mounted, as indicated in FIG. 4, to a beam in such a way that they can reproduce images of the upper corners 6 and/or 7 of an insulating glass pane 1.

In case of recorders consisting of two TV cameras, the arrangement is preferably such that the viewing directions 13, 13' in each case are directed to the opposite rim of the edge joint, i.e. the rim of the sealing compound lying farther remote from the camera (the viewing directions 13, 13' thus intersect each other). In this way, two mutually complementary recordings are produced by the recorders 12 with two TV cameras which can be displayed side-by-side, optionally also as a single picture, on a monitor, such as monitor 41.

In sun, nation, the invention can be described, for example, as follows:

An apparatus is disclosed for carrying away sealed insulating glass panes with a conveying device wherein the conveying device is associated, in the zone of the end on the inlet side and the end on the outlet side, with recorders, preferably those with respectively two TV cameras, producing images of the corners of the insulating glass pane, these images being displayed as stationary images on a monitor until the subsequent insulating glass pane arrives. In order to improve the quality of the images, illuminating devices are associated with the recorders, these devices being activated only when the recorders are in operation. Based on the images of the corners of the insulating glass pane produced by the recorders and displayed on the monitor, the quality of the seal in the zone of the corners can be evaluated even without lifting out and turning of insulating glass panes.

What is claimed is:

1. Apparatus for inspecting the seal of insulating glass panes (1) in the zone of corners (4, 5, 6, 7) of an insulating glass pane (1), comprising at least one TV camera (12), located in the region of a delivery conveyor (3, 14) of a sealing facility for insulating glass panes, and at least one monitor (41) connected to the at least one camera (12) for displaying the stationary recorded images of corners (4, 5, 6, 7) of an insulating glass pane (1) recorded by the camera (12), the at least one camera (12) being provided in an interruption (16) beside the beginning (10) of the delivery conveyor (3, 14) through which a sealing nozzle (50) moves from a ready position into an operative position.

2. Apparatus according to claim 1, wherein said at least one camera (12) is located at a lower level than the delivery conveyor (3, 14).

3. Apparatus according to claim 1, wherein said at least one camera (12) is mounted with a viewing direction (13) forming an acute angle with the plane of the insulating glass pane (1).

4. Apparatus according to claim 1, wherein at least one additional camera (12) is provided for producing images of the upper corners (6, 7) of the sealed insulating glass panes (1).

5. Apparatus according to claim 1, wherein the thus-produced images are displayed and retained on the monitor (41) until the next insulating glass pane (1) arrives to be sealed.

6. Apparatus according to claim 1, wherein a device (39) is provided for detecting the arrival of the next insulating glass pane to be sealed, this device triggering the clearing of the image displayed on the monitor (41), of corners (4, 5, 6, 7) of the previously sealed insulating glass pane (1).

7. Apparatus according to claim 1, and a further TV camera (12) in the region of the end (11) on the outlet side of the delivery conveyor (3, 14) of the sealing facility.

8. Apparatus according to claim 7, wherein the camera (12) located in the region of the sealing nozzle (50) is associated with a lid protecting the optical system of this camera, this lid being opened exclusively during production of an image.

9. Apparatus according to claim 1, wherein a control unit (25, 30) is provided which triggers the production of an image by the at least one camera (12) located in the zone of the end (10) of the delivery conveyor (3, 14) on the inlet side when the insulating glass pane (1) is at a standstill after termination of the sealing process and prior to beginning of the carrying-away step by the delivery conveyor (3, 14).

10. Apparatus according to claim 9, wherein the control unit (30) comprises a device (25) for detecting the insulating glass pane (1), which controls the camera (12) when the corner (4) of the insulating glass pane (1) to be imaged thereby, at the rear as based on the conveying direction (arrow 49), is located in the zone of the end (10) of the delivery conveyor (3, 14) on the inlet side.

11. Apparatus according to claim i, wherein a control unit (25, 30) is provided which triggers the production of an image by the at least one camera (12) located at the end (11) of the delivery conveyor (3, 14) on the outlet side when the insulating glass pane (1) is in a removal position at the end (11) of the delivery conveyor (3, 14)

12. Apparatus according to claim 11, wherein the control unit comprises a device (25) for detecting the insulating glass pane (1), which controls the camera (12) when the corner (5) of the insulating glass pane (1) to be imaged thereby, at the front as based on the conveying direction (arrow 49), is located in the zone of the end (11) of the delivery conveyor (3, 14) on the outlet side.

13. Apparatus according to claim 1, wherein at least one illuminating device (15) is associated with the camera (12), this device illuminating the corner (4, 5, 6, 7) to be imaged at an angle different from the angle formed by the viewing direction (13) of the camera (12) with the plane of the insulating glass pane (1).

14. Apparatus according to claim 13, wherein the illuminating device (15) comprises a flash unit as a light source.

15. Apparatus according to claim 13, wherein the camera (12) and the illuminating devices (15) associated therewith are mounted on a beam (9) that can be adjusted upward and downward and carries freely rotatable rollers (7), the upper rim of the sealed insulating glass pane (1) leaning against these rollers.

16. Apparatus according to claim 13, wherein the illuminating device (15) is coupled with a control unit (30) of the camera (12) with inclusion of a device (25) for detecting the presence of an insulating glass pane (1), the illuminating device 915) being turned on only while the camera operates.

17. Apparatus according to claim 1, wherein said at least one camera consists of two TV cameras (51) mounted with viewing directions (13, 13') different from each other with respect to the plane of the insulating glass pane (1).

18. Apparatus according to claim 17, wherein the two TV cameras (51) are mounted with viewing directions (13, 13') forming acute angles with the plane of the insulating glass pane (1).

19. Apparatus according to claim 17, wherein the TV cameras (51) are mounted with viewing directions oriented substantially symmetrically to the plane of the insulating glass pane (1).

20. Apparatus according to claim 17, wherein the TV cameras (51) are mounted so that their viewing direction (13, 13') is oriented to the respectively oppositely located rim of the seal of the insulating glass pane.

* * * * *